(12) United States Patent
Reaume et al.

(10) Patent No.: US 7,776,870 B2
(45) Date of Patent: Aug. 17, 2010

(54) METHODS FOR MODULATING LYN KINASE ACTIVITY AND TREATING RELATED DISORDERS

(75) Inventors: Andrew Reaume, Exton, PA (US); Michael S. Saporito, Exton, PA (US)

(73) Assignee: Melior Pharmaceuticals I, Inc., Exton, PA (US)

( * ) Notice: Subject to any disclaimer, the term of this patent is extended or adjusted under 35 U.S.C. 154(b) by 0 days.

(21) Appl. No.: 11/507,652

(22) Filed: Aug. 22, 2006

(65) Prior Publication Data

US 2007/0093516 A1    Apr. 26, 2007

Related U.S. Application Data

(60) Provisional application No. 60/709,798, filed on Aug. 22, 2005, provisional application No. 60/808,533, filed on May 26, 2006.

(51) Int. Cl.
*A61K 31/505* (2006.01)
*A61K 31/515* (2006.01)
*A61K 31/425* (2006.01)

(52) U.S. Cl. ............ 514/269; 514/270; 514/274; 514/369; 514/866; 514/909

(58) Field of Classification Search .......... 514/269, 514/270, 274, 909, 866, 369; 515/866
See application file for complete search history.

(56) References Cited

U.S. PATENT DOCUMENTS

| | | | |
|---|---|---|---|
| 3,922,345 A * | 11/1975 | Lipinski et al. | ......... 514/269 |
| 4,080,454 A | 3/1978 | Lipinski et al. | |
| 4,824,851 A | 4/1989 | Takaya et al. | |
| 5,476,855 A | 12/1995 | Kouni et al. | |
| 5,698,155 A | 12/1997 | Grosswald et al. | |
| 5,721,114 A | 2/1998 | Abrahamsen et al. | |
| 5,721,241 A | 2/1998 | Kouni et al. | |
| 6,004,925 A | 12/1999 | Dasseux et al. | |
| 6,037,323 A | 3/2000 | Dasseux et al. | |
| 6,410,255 B1 | 6/2002 | Pollok et al. | |
| 2002/0151497 A1 | 10/2002 | Ben-Sasson | |
| 2005/0009817 A1 | 1/2005 | Savoy et al. | |
| 2006/0252777 A1 | 11/2006 | Kim et al. | |
| 2007/0049609 A1 | 3/2007 | Broka et al. | |
| 2007/0093516 A1 | 4/2007 | Reaume et al. | |
| 2007/0185070 A1 | 8/2007 | Pershadsingh | |

FOREIGN PATENT DOCUMENTS

| | | |
|---|---|---|
| CN | 1395560 A | 2/2003 |
| GB | 1377308 | 12/1974 |
| WO | 94/01414 | 1/1994 |
| WO | 01/51463 A1 | 7/2001 |

OTHER PUBLICATIONS

Masuda et al., "Peptic Ulcer in Diabetes Mellitus", Gastroenterologia Japonica, vol. 11, No. 1, pp. 1-4 (1976).*

Briggs, S.D. et al., "Affinity of Src Family Kinase SH3 Domains for HIV Nef in Vitro Does Not Predict Kinase Activation by Nef in Vivo." Biochemistry 39: 489-495 (2000).

Ishikawa, H. et al., "Requirements of src family kinase activity associated with CD45 for myeloma cell proliferation by interleukin-6." Blood 99: 2172-2178 (2002).

Reaven, Role of insulin resistance in human disease (syndrome X): an expanded definition, Annu Rev Med (1993) 44:121-131.

Blasioli, J. et al., Lyn/CD22/SHP-1 and their importance in autoimmunity, Curr. Dir. Autoimmun. 5: 151-160 (2002).

Langer, R., New methods of drug delivery, Science vol. 249, Issue 4976, 1527-1533 (1990).

Treat et al., Liposomes in the Therapy of Infectious Disease and Cancer, Lopez-Berestein and Fidler (eds.), Liss, New York, pp. 353-365 (1989).

Lopez-Berestein, G., Treatment of Systemic Fungal Infections with Liposomal-Amphotericin B, 1989 ibid., pp. 317-327.

Sefton, Michael V., Implantable Pumps, CRC Crit. Ref. Biomed. Eng., 1987;14(3):201-40.

Buchwald, Henry, et al., Long-tern, continuous intravenous heparin administration by an implantable infusion pump in ambulatory patients with recurrent venous thrombosis, Surgery, Oct. 1987;88(4):507-16.

Langer and Wise (eds.) "Medical Applications of Controlled Release," CRC Pres., Boca Raton, Fla. (1974).

(Continued)

*Primary Examiner*—Kevin Weddington
(74) *Attorney, Agent, or Firm*—Pepper Hamilton LLP

(57) ABSTRACT

The present invention relates to compounds and pharmaceutically acceptable salts thereof and formulations comprising the compounds or a pharmaceutically acceptable salts thereof that are useful in modulating lyn kinase activity. In particular, the compounds or a pharmaceutically acceptable salts thereof are useful for treating or preventing a disease or disorder including cardiovascular disease, dyslipidemia, dyslipoproteinemia, a disorder of glucose metabolism, metabolic syndrome (i.e., Syndrome X), a peroxisome proliferator activated receptor-associated disorder, septicemia, a thrombotic disorder, type II diabetes, obesity, pancreatitis, hypertension, renal disease, inflammation, or impotence.

18 Claims, 8 Drawing Sheets

OTHER PUBLICATIONS

Smolen and Ball (eds.), "Controlled Drug Bioavailability, Drug Product Design and Performance," Wiley, New York (1984).

Langer, Robert and Peppas, Nikolaos, Chemical and Physical Structure of Polymers as Carriers for Controlled Release of Bioactive Agents: A Review, JMS-Rev. Macromol. Chem. Phys., 1983; 23(1):61-126.

Levy, R. J. et al., Inhibition of calcification of bioprosthetic heart valves by local controlled-release diphosphonate, Science vol. 228, Issue 4696, pp. 190-192 (1985).

During, Matthew J., et al., Controlled Release of Dopamine from a Polymeric Brain Implant: In Vivo Characterization, Annals of Neurology, Apr. 1989; 25(4):351-56.

Howard, Matthew A., III, et al., Intracerebral drug delivery in rats with lesion-induced memory deficits, J. Neurosurg., Jul. 1989; 71:105-112.

Goodson, "Medical Applications Controlled Release" supra [J. Neurosurg.], vol. 2, pp. 115-138 (1984).

Lipinski, C. A. et al., Bronchodilator and Antiulcer Phenoxypyrimidiones, J. Med. Chem. 1980; 23:1026-1031.

Muller, G., et al., Interaction of phosphatidylinositolglycan(-peptides) with plasma membrane lipid rafts triggers insulin-mimetic signaling in rat adipocytes, Archives of Biochemistry and Biophysics, 2002;408:7-16.

Z-Lyte Kinase Assay Kits, Invitrogen website http://www.invitrogen.com, 2008.

International Search Report dated Jul. 25, 2008 for PCT/US2008/054361.

International Search Report dated Feb. 26, 2007 for PCT/US2006/032788.

International Search Report dated Oct. 6, 2008 for PCT/US2008/070739.

International Search Report dated Sep. 1, 2009 for PCT/US2009/049509.

* cited by examiner

Figure 1 – Compound 102 Oral Glucose tolerance
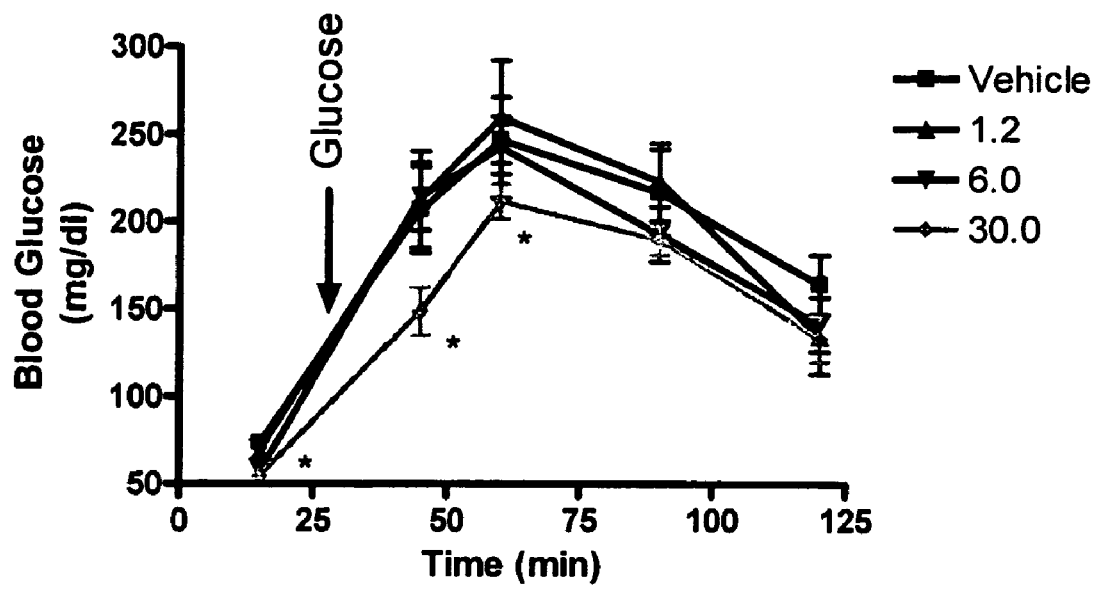
Figure 2. Compound 102 - Oral Glucose Tolerance
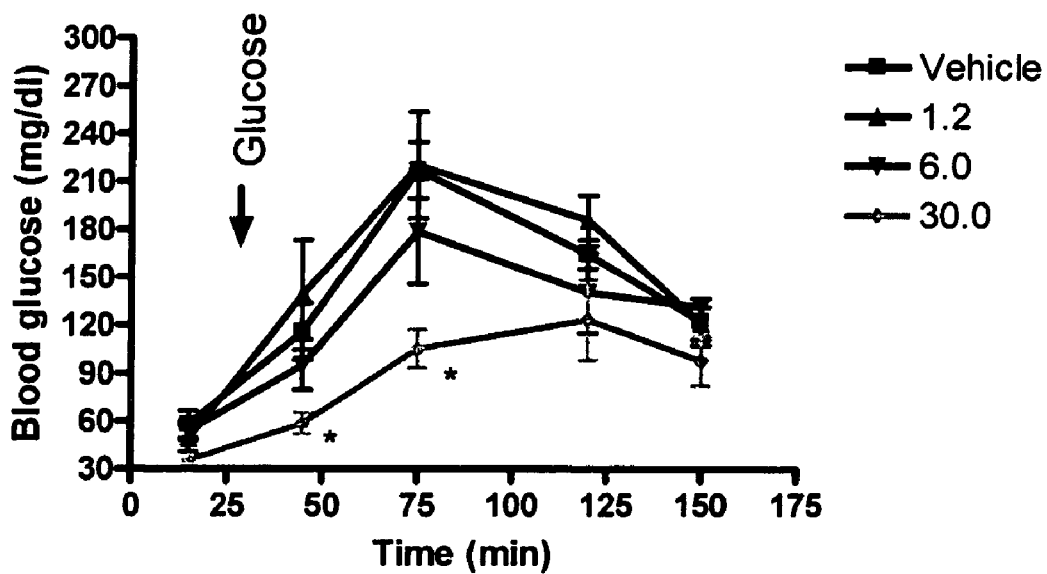

Figure 3 - Compound 105 - Oral Glucose Tolerance Test
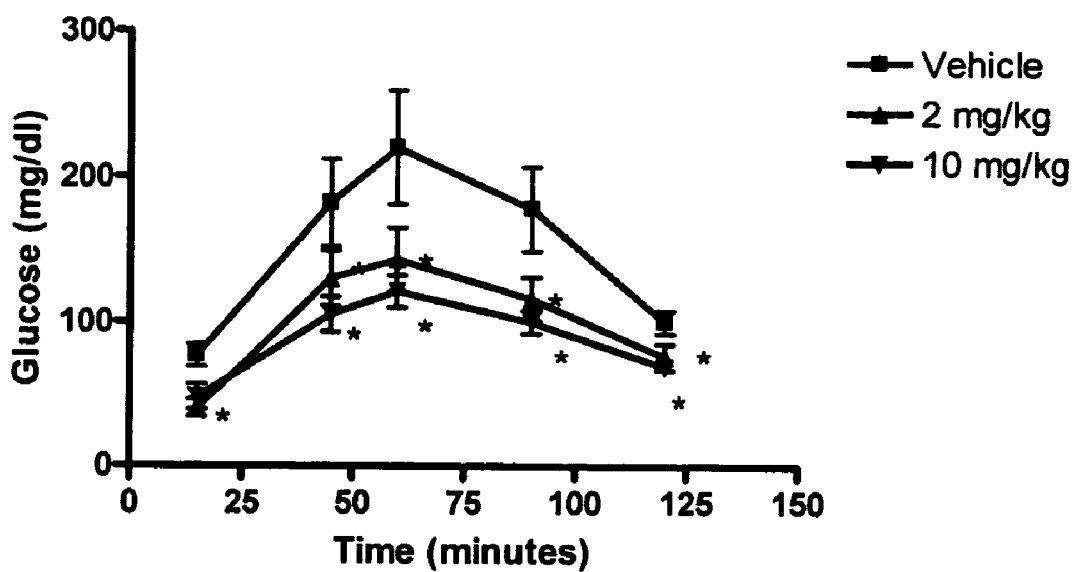
Figure 4 - Compound 102 - Western Diet
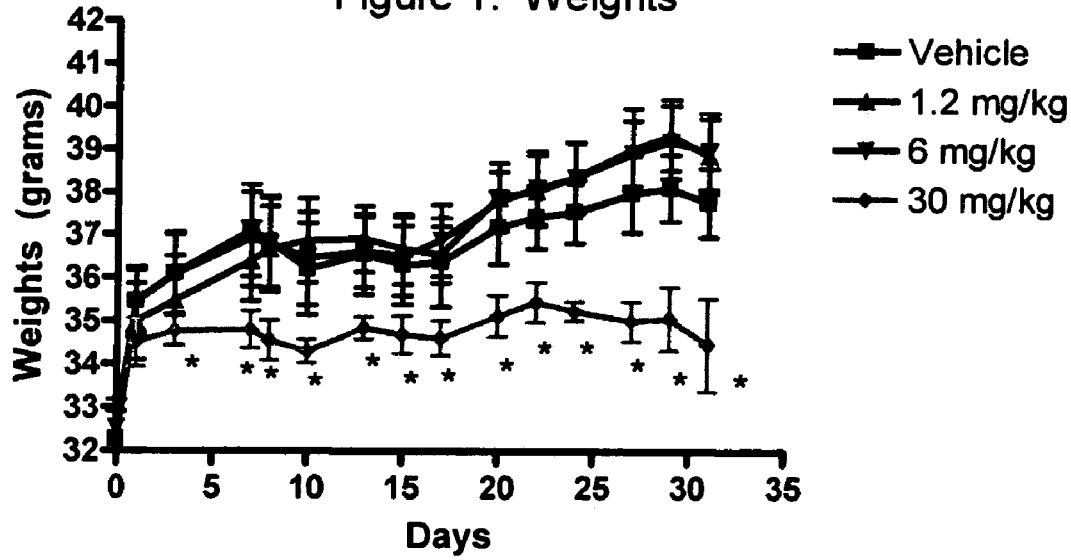

Figure 5 - Compound 102 - Western Diet Food Intake
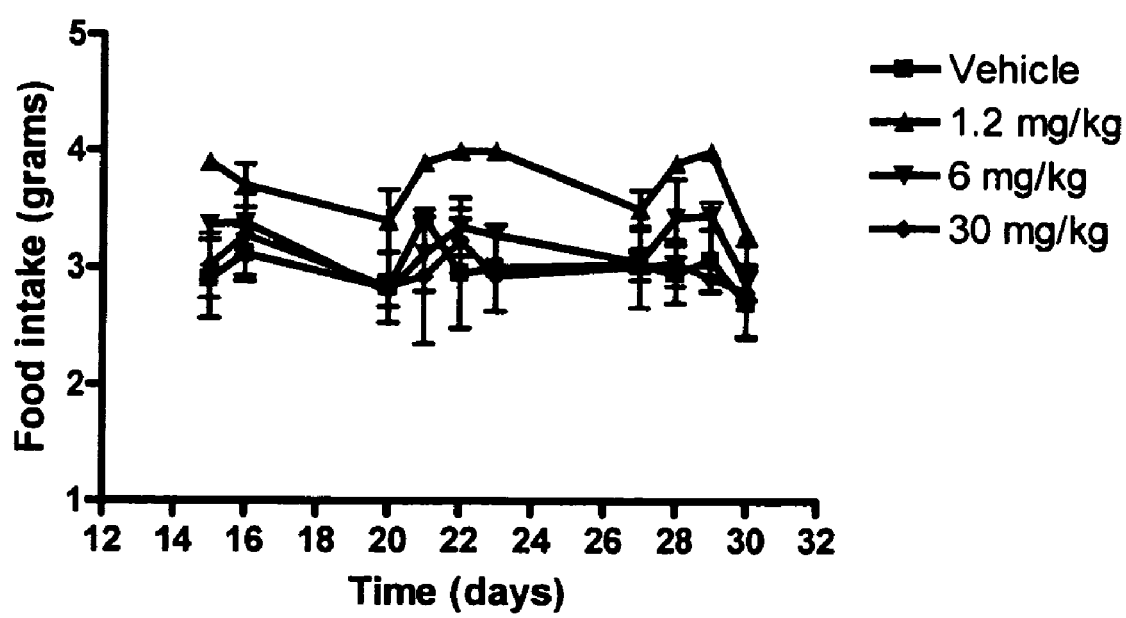

Figure 6 - Fat Pad Weights
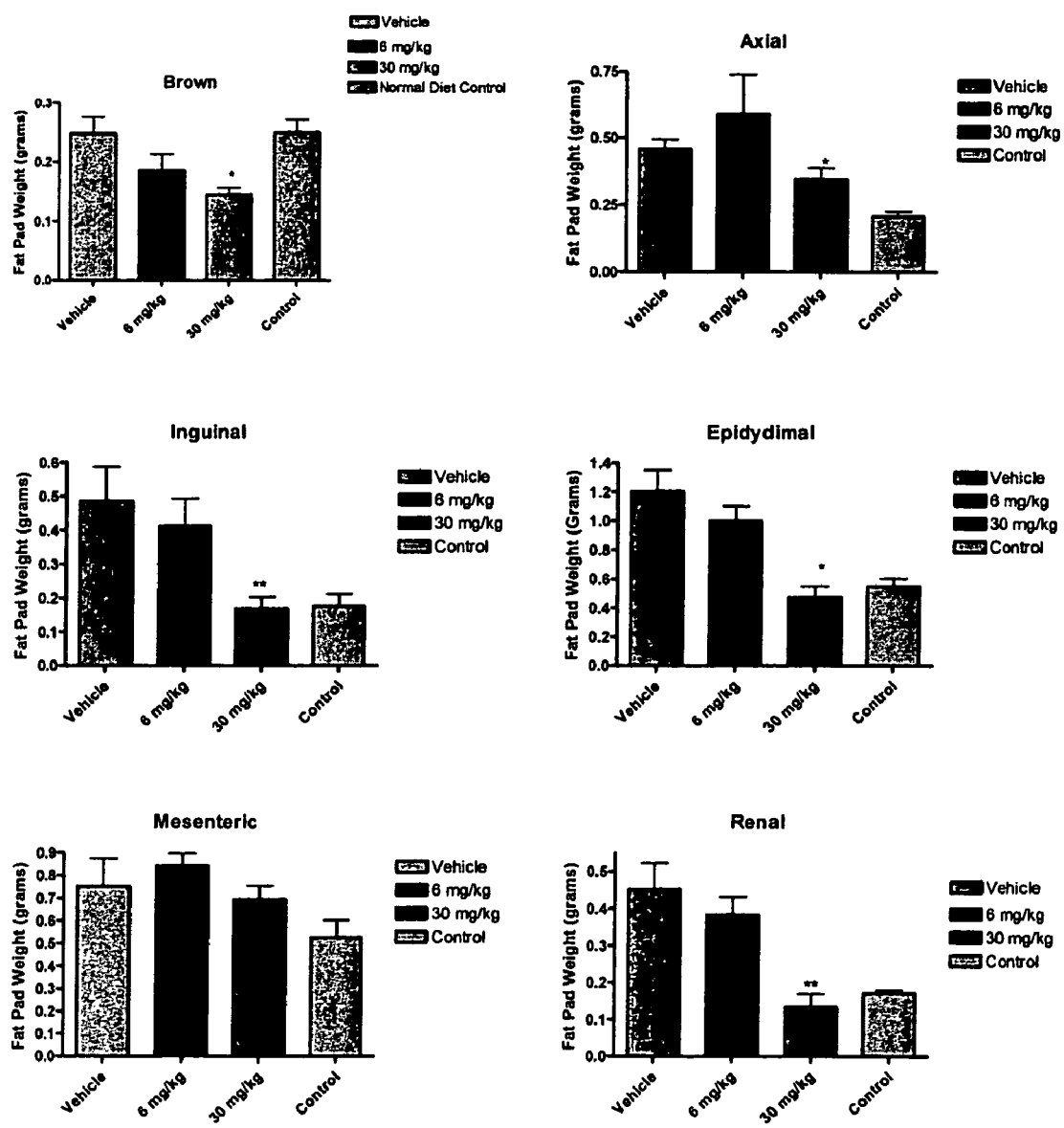

Figure 7 - Compound 102 - Leptin Levels
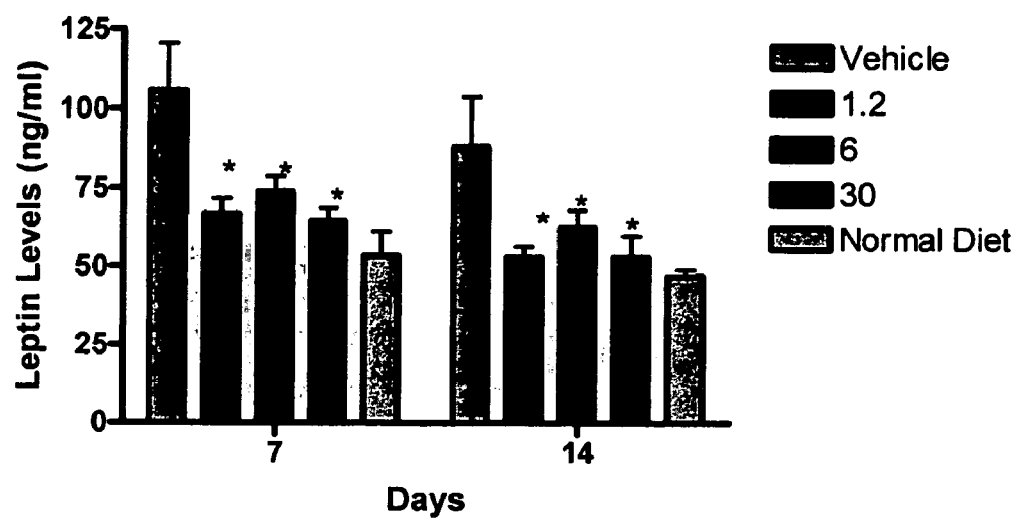
Figure 8 – Compound 102 - Reduces weight gain in Db/Db mice without affecting food intake.
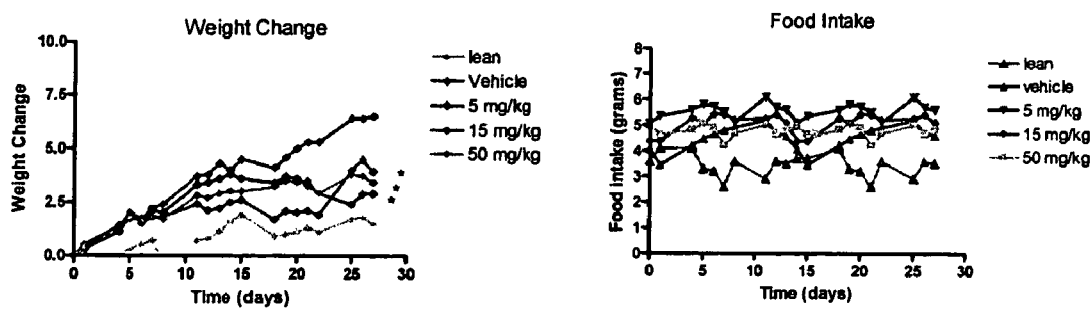

Figure 9 – Compound 102 - Lowers blood glucose levels in DB/DB mice with a single acute administration.
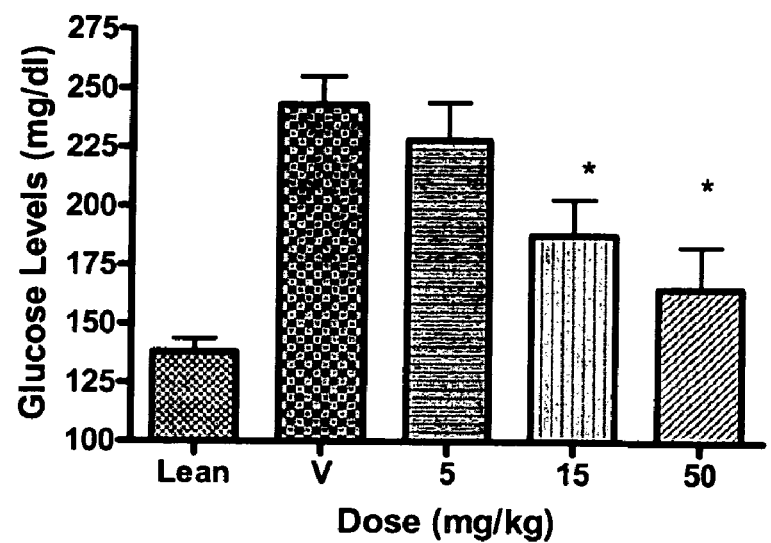

Figure 10 – Compound 102 – Reduction in weight gain in Db/Db mice without affecting food intake.
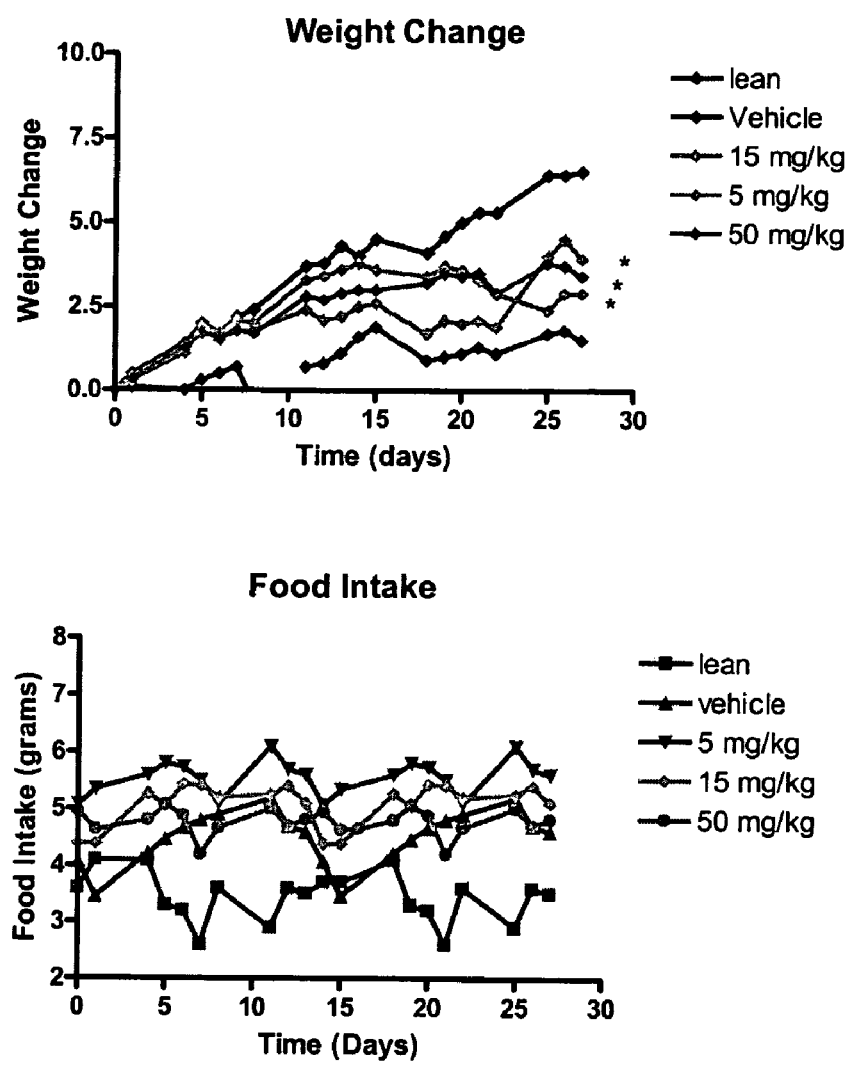

Figure 11 – Compound 102 – Reduction in Blood Glucose Levels in Zucker Rats Challenged with a High Oral Glucose solution
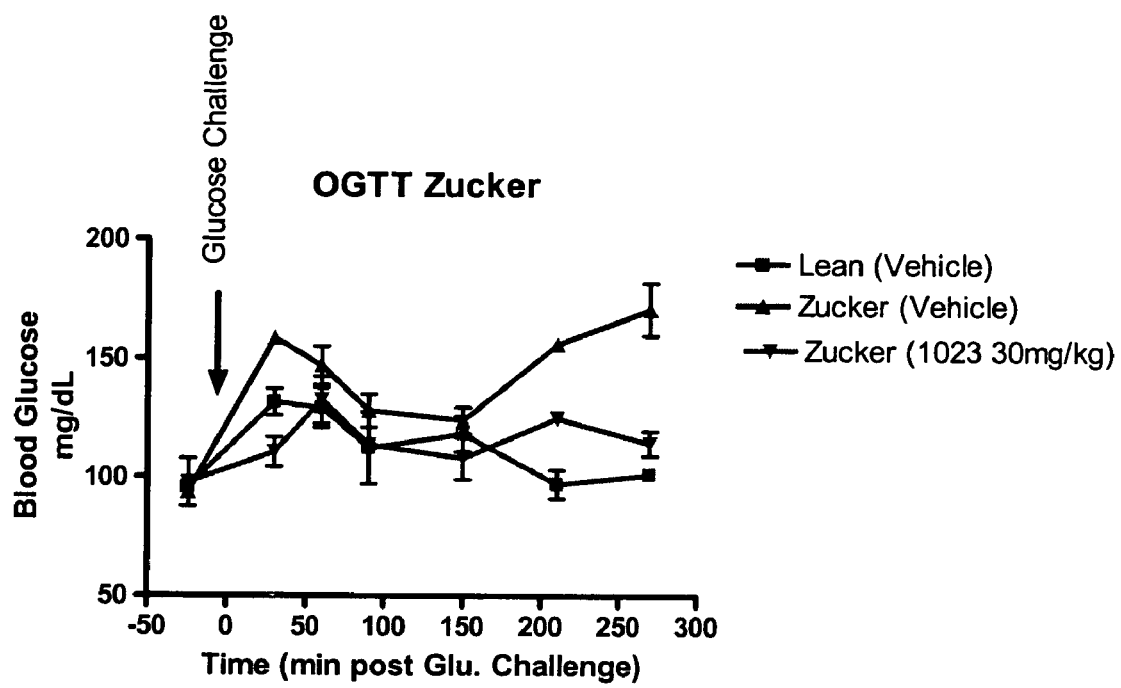
Figure 12 – Compound 102 - Activation of Lyn kinase *in vitro*
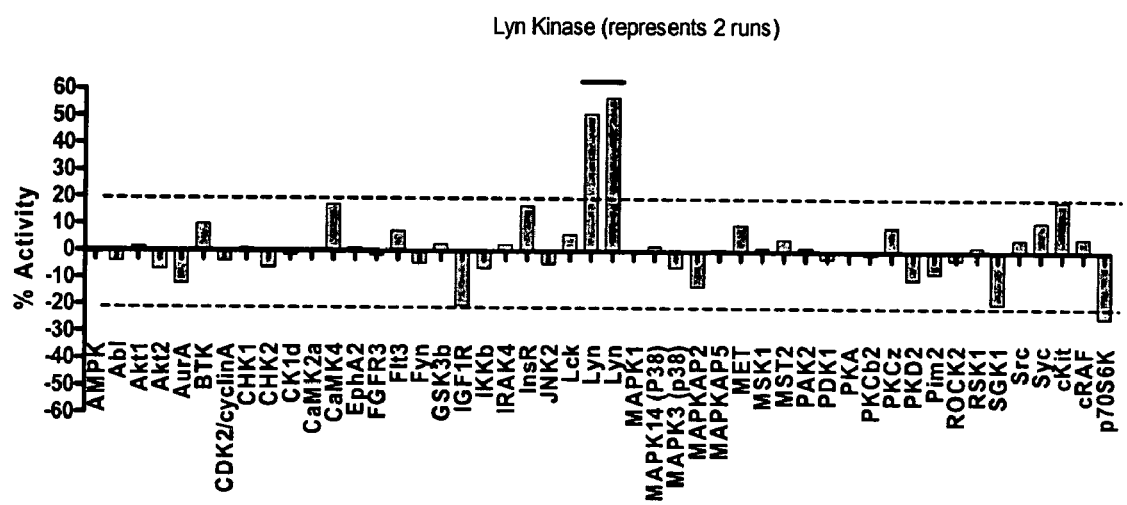

METHODS FOR MODULATING LYN KINASE ACTIVITY AND TREATING RELATED DISORDERS

CROSS-REFERENCE TO RELATED APPLICATIONS

This application claims the benefit of U.S. provisional patent application No. 60/709,798, filed Aug. 22, 2005, and U.S. provisional patent application No. 60/808,533, filed May 26, 2006, each which is incorporated herein by reference in its entirety.

1. FIELD OF THE INVENTION

The present invention relates to compositions and formulations comprising therapeutically or prophylactically active compounds or pharmaceutically acceptable salts thereof, methods for modulating the activity of Lyn kinase and methods for treating disorders associated with Lyn kinase. In particular, the formulation are useful for treating or preventing diseases and disorders including cardiovascular disease, dyslipidemia, dyslipoproteinemia, a disorder of glucose metabolism, metabolic syndrome (i.e., Syndrome X), a peroxisome proliferator activated receptor-associated disorder, septicemia, a thrombotic disorder, type II diabetes, cancer, obesity, pancreatitis, hypertension, renal disease, inflammation, or impotence, comprising administering a composition comprising a therapeutically or prophylactically effective amount of a compound of the invention or a pharmaceutically acceptable salt thereof.

2. BACKGROUND OF THE INVENTION

Lyn kinase is a member of the src family of non-receptor protein tyrosine kinases that is predominantly expressed in B-lymphoid and myeloid cells. See, e.g., Briggs S D, Lerner E C, Smithgall T E: Affinity Of Src Family Kinase SH3 Domains For HIV Nef In Vitro Does Not Predict Kinase Activation By Nef In Vivo. Biochemistry 39: 489-495 (2000), incorporated herein by reference. Lyn participates in signal transduction from cell surface receptors that lack intrinsic tyrosine kinase activity. Activation of the lyn kinase activity is necessary for proliferation of CD45+ myeloma cells stimulated by IL-6. See, e.g., Ishikawa H, Tsuyama N, Abroun S, Liu S, Li F J, Taniguchi O, Kawano M M: Requirements of src family kinase activity associated with CD45 for myeloma cell proliferation by interleukin-6. Blood 99: 2172-2178 (2002), incorporated herein by reference. Association of lyn and fyn with the proline-rich domain of glycoprotein VI regulates intracellular signaling. See, e.g., Suzuki-Inoue K, Tulasne D, Shen Y, Bori-Sanz T, Inoue O, Jung S M, Moroi M, Andrews R K, Berndt M C, Watson S P: Association of Fyn and Lyn with the proline-rich domain of glycoprotein VI regulates intracellular signaling. J. Biol. Chem. 277: 21561-21566 (2002), incorporated herein by reference. The lyn/CD22/SHP-1 pathway is important in autoimmunity. See, e.g., Blasioli J, Goodnow C C: Lyn/CD22/SHP-1 and their importance in autoimmunity. Curr. Dir. Autoimmun. 5: 151-160 (2002), incorporated herein by reference.

Obesity, hyperlipidemia, and diabetes have been shown to play a causal role in various disorders including, for example, atherosclerotic cardiovascular diseases, which currently account for a considerable proportion of morbidity in Western society. One human disorder, termed "Syndrome X" or "Metabolic Syndrome," is manifested by defective glucose metabolism (e.g., insulin resistance), elevated blood pressure (i.e., hypertension), and a blood lipid imbalance (i.e., dyslipidemia). See e.g. Reaven, 1993, *Annu. Rev. Med.* 44:121-131.

None of the currently commercially available drugs for modulating lyn kinase or managing elevated glucose levels have a general utility in regulating lipid, lipoprotein, insulin and glucose levels in the blood. Thus, compounds that have one or more of these utilities are clearly needed. Furthermore, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by glucose metabolism and/or elevated glucose levels.

3. SUMMARY OF THE INVENTION

The invention encompasses agents that are useful in modulating the activity of lyn kinase. In particular, the agents useful in modulating the activity of lyn kinase include, but are not limited to compositions and formulations comprising a compound of Formulas I-VII. In an illustrative embodiment, the agents up-regulate the activity and/or expression of lyn kinase. Thus, surprisingly the compounds of the invention act as activators or agonists of lyn kinase. Thus, the compounds of the invention direct the modulation of lyn kinase in the insulin receptor pathway (i.e., lyn activation has insulin receptor activation-like activity).

The invention also encompasses methods for treating or preventing a disease or disorder including, but not limited to, cardiovascular disease, dyslipidemia, reducing fat depot levels, dyslipoproteinemia, a disorder of glucose metabolism (i.e., elevated blood glucose levels), metabolic syndrome (i.e., Syndrome X), a PPAR-associated disorder, septicemia, a thrombotic disorder, type II diabetes, cancer, obesity, pancreatitis, hypertension, a renal disease, inflammation, and impotence comprising administering to a subject, preferably a mammal, in need thereof a therapeutically or prophylactically effective amount of a composition or formulation comprising a compound of the invention.

The invention further encompasses methods for reducing blood glucose levels, reducing fat depot levels and for treating or preventing a cardiovascular disease, dyslipidemia, dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, and impotence, which comprises administering to a mammal in need of such treatment or prevention a therapeutically or prophylactically effective amount of a composition comprising a compound of Formula I-VI, or a pharmaceutically acceptable salt or prodrug thereof, and a pharmaceutically acceptable vehicle.

In a preferred embodiment, the composition comprising a compound of the invention are for the use in treating or preventing metabolic syndrome or Syndrome X or the treatment of disorders associated with these syndromes including, but not limited to, obesity, prediabetes, and type II diabetes as well as complications of obesity and diabetes. Complications of obesity include, but are not limited to, hypercholesterolemia, hypertension, and coronary heart disease. Complications of diabetes include, but are not limited to, diabetic neuropathy, diabetic retinopathy, erectile dysfunction, and kidney disease.

As described herein, the compositions that are useful in the methods of the invention encompass compounds of Formulas I-VII.

In one embodiment, the invention encompasses compositions comprising a compound of formula (I):

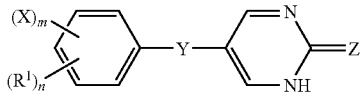

or pharmaceutically acceptable salts and prodrugs thereof, wherein $R^1$ is an alkyl group; X is a halogen; Y is O, S, or NH; Z is O or S; n is an integer from 0 to 5 and m is an integer from 0 to 5, wherein m+n is less than or equal to 5.

In one embodiment, the alkyl group is methyl and n is 1. In another embodiment, the halogen is chlorine and m is 1. In another embodiment, Y is O. In another embodiment, the Z is O.

In a preferred embodiment, $R_1$ is methyl, Y is O, Z is O, n is 1, and m is 0, more preferably $R_1$ is in the meta position.

In another preferred embodiment, X is chlorine, Y is O, Z is O, n is 0, and m is 1, more preferably X is in the meta position. In another preferred embodiment, the mammal is a human. In another preferred embodiment, the effective amount is from about 0.1 mg to about 100 mg/kg, preferably the administration is oral.

In another embodiment, the invention encompasses compositions comprising a compound of formula (II):

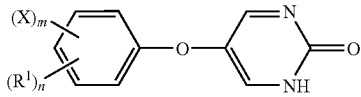

or pharmaceutically acceptable salts and prodrugs thereof, wherein $R^1$ is an alkyl group; X is a halogen; n is an integer from 0 to 5 and m is an integer from 0 to 5, wherein m+n is less than or equal to 5.

In yet another embodiment, the invention encompasses compositions comprising a compound of formula (III):

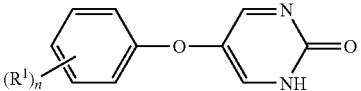

or pharmaceutically acceptable salts and prodrugs thereof, wherein $R^1$ is an alkyl-group and n is an integer from 0 to 5.

In another embodiment, the invention encompasses compositions comprising a compound of formula (III):

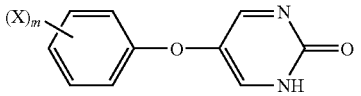

or pharmaceutically acceptable salts and prodrugs thereof, wherein X is a halogen and m is an integer from 0 to 5.

In another embodiment, the invention encompasses compositions comprising a compound of formula (V):

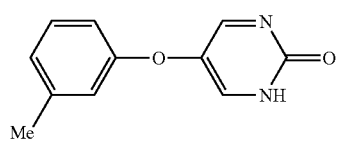

or pharmaceutically acceptable salts and prodrugs thereof.

In another embodiment, the invention encompasses compositions comprising a compound of formula (VI):

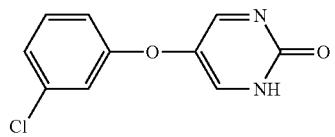

or pharmaceutically acceptable salts and prodrugs thereof.

The present invention may be understood more fully by reference to the figures, detailed description, and examples, which are intended to exemplify non-limiting embodiments of the invention.

4. BRIEF DESCRIPTION OF THE DRAWINGS

FIG. 1 illustrates oral glucose tolerance of Compound 102 by administering Compound 102 once at the indicated doses prior to glucose administration. Blood glucose levels were measured at the indicated times.

FIG. 2 illustrates oral glucose tolerance of Compound 102 by administering Compound 102 four times at 30 minute intervals at the indicated doses prior to glucose administration. Blood glucose levels were measured at the indicated times.

FIG. 3 illustrates oral glucose tolerance of Compound 102 by administering Compound 105 once at the indicated doses prior to glucose administration. Blood glucose levels were measured at the indicated times.

FIG. 4 illustrates weight gain of animals administered Compound 102. Animals were weighed every other day for the duration of the study.

FIG. 5 illustrates food intake of animals administered Compound 102. Food weight was monitored every day beginning on day 14 of the western diet.

FIG. 6 illustrates fat pad weights of animals administered Compound 102. At the end of the Western diet study (day 31), animals were sacrificed and fat pads weighed FIG. 7 illustrates leptin levels of animals administered Compound 102. Mice on western diet were analyzed for leptin on days 7 and 14 of the diet.

FIG. 8 illustrates weight changes in Db/Db mice, which were dosed with Compound 102 at the indicated doses bid (twice/day). Weight changes and food intake were monitored over the course of the study (28 days). Compound 102 significantly lowered weight gain without affecting food intake.

FIG. 9 illustrates reduction in glucose levels in db/db mice after an acute injection of Compound 102. The glucose levels were measured after the first treatment of the chronic study. Glucose levels were measured 2 hrs after drug administration.

FIG. 10 illustrates reduction in weight gain in Db/Db mice administered Compound 102 without affecting food intake.

FIG. 11 illustrates reduction is blood glucose levels in Zucker Rats administered Compound 102 and challenged with a high oral glucose solution. At 12 weeks of age, Zucker rats were administered Compound 102 at a concentration of 30 mg/kg (ip). Blood glucose levels were measured 30 minutes after administration. Forty-five minutes after drug.

FIG. 12 illustrates increased in vitro activity in the Lyn Kinase enzyme demonstrated by Compound 102.

5. DETAILED DESCRIPTION OF THE INVENTION

5.1. Definitions

As used herein and unless otherwise indicated, the phrase "altering lipid metabolism" indicates an observable (i.e., measurable) change in at least one aspect of lipid metabolism including, but not limited to, total blood lipid content, blood HDL cholesterol, blood LDL cholesterol, blood VLDL cholesterol, blood triglyceride, blood Lp(a), blood apo A-I, blood apo E or blood non-esterified fatty acids.

As used herein and unless otherwise indicated, the phrase "altering glucose metabolism" indicates an observable (i.e., measurable) change in at least one aspect of glucose metabolism including, but not limited to, total blood glucose content, blood insulin, the blood insulin to blood glucose ratio, insulin sensitivity, or oxygen consumption.

As used herein and unless otherwise indicated, the term "alkoxy group" means an —O-alkyl group, wherein alkyl is as defined herein. An alkoxy group can be unsubstituted or substituted with one or two suitable substituents. Preferably, the alkyl chain of an alkyloxy group is from 1 to 6 carbon atoms in length, referred to herein, for example, as "$(C_1-C_6)$ alkoxy."

As used herein and unless otherwise indicated, the term "alkyl" or "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl."

As used herein and unless otherwise indicated, the term "aryloxy group" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy."

As used herein, the term "benzyl" means —$CH_2$-phenyl.

As used herein, the term "carbonyl" group is a divalent group of the formula —C(O)—.

As used herein and unless otherwise indicated, the term "compounds of the invention" means, collectively, the compounds of formulas I, II, III, IV, V, and VI and pharmaceutically acceptable salts thereof. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomersl by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein, the terms "diabetes" and "type II diabetes" are used interchangeably and include, but are not limited to, non-insulin dependent diabetes mellitus, diabetes insipidus, and are related to insulin resistance (i.e., lack of the ability of the body to respond to insulin appropriately) and is often accompanied by related complications including, for example, obesity and high cholesterol.

As used herein, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the term "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$ heteroaryl."

As used herein and unless otherwise indicated, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $(C_1-C_6)$heterocycloalkyl.

As used herein and unless otherwise indicated, the term "heterocyclic radical" or "heterocyclic ring" means a heterocycloalkyl group or a heteroaryl group.

As used herein and unless otherwise indicated, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. Preferably, the hydrocarbon chain of a hydrocarbyl group is from 1 to 6 carbon atoms in length, referred to herein as "$(C_1-C_6)$hydrocarbyl."

When administered to a mammal (e.g., to an animal for veterinary use or to a human for clinical use) the compounds of the invention are administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 90% preferably at least 95%, more preferably at least 98%, and most preferably at least 99% of a compound of the invention by weight of the isolate.

As used herein and unless otherwise indicated, the term "lyn kinase related disorder" refers to any disorder in a mammal including humans, associated with the altered expression and/or activity of lyn kinase including, but not limited to, cardiovascular disease, dyslipidemia, reducing fat depot levels, dyslipoproteinemia, a disorder of glucose metabolism (i.e., elevated blood glucose levels), metabolic syndrome (i.e., Syndrome X), a PPAR-associated disorder, septicemia, a thrombotic disorder, diabetes, obesity, pancreatitis, hypertension, a renal disease, inflammation, and impotence.

As used herein and unless otherwise indicated, the term "modulate" refers to a change in the expression and/or activity of a protein, preferably an enzyme, more preferably lyn kinase. In an illustrative embodiment, "modulate" refers to increase or decrease the expression and/or activity of a protein, preferably an enzyme, more preferably lyn kinase.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

The term "phenyl" means —$C_6H_5$. A phenyl group can be unsubstituted or substituted with one or two suitable substituents.

As used herein, "pre-diabetes" refers to symptoms of diabetes wherein the patient exhibits elevated glucose levels but the full onset of disorders associated with type II diabetes has not yet manifested itself.

As used herein, a "suitable substituent" means a group that does not nullify the synthetic or pharmaceutical utility of the compounds of the invention or the intermediates useful for preparing them. Examples of suitable substituents include, but are not limited to: $(C_1-C_8)$alkyl; $(C_1-C_8)$alkenyl; $(C_1-C_8)$alkynyl; $(C_6)$aryl; $(C_3-C_5)$heteroaryl; $(C_3-C_7)$cycloalkyl; $(C_1-C_8)$alkoxy; $(C_6)$aryloxy; —CN; —OH; oxo; halo, —$NO_2$; —$CO_2H$; —$NH_2$; —NH($(C_1-C_8)$alkyl); —N(($C_1$-$C_8$)alkyl)$_2$; —NH($(C_6)$aryl); —N($(C_6)$aryl)$_2$; —CHO; —CO(($C_1$-$C_8$)alkyl); —CO($(C_6)$aryl); —$CO_2$(($C_1$-$C_8$)alkyl); and —$CO_2$($(C_6)$aryl). One of skill in art can readily choose a suitable substituent based on the stability and pharmacological and synthetic activity of the compound of the invention.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated. In one embodiment, the phrase "therapeutically effective amount" of a composition of the invention is measured by the therapeutic effectiveness of a compound of the invention to alter the expression and/or activity of lyn kinase including, but not limited to up- and down-regulation of this protein. Surprisingly, the inventors have found that therapeutically effective amounts of the compounds of the invention up-regulate the expression and/or activity of lyn kinase.

5.2 Compounds of the Invention

As set forth herein, the invention encompasses methods for treating or preventing a cardiovascular disease, dyslipidemia, dyslipoproteinemia, a disorder of glucose metabolism, Syndrome X, a PPAR-associated disorder, septicemia, a thrombotic disorder, type II diabetes, obesity, pancreatitis, hypertension, a renal disease, inflammation, and impotence, which comprises administering to a mammal in need of such treatment or prevention a therapeutically or prophylactically effective amount of a composition comprising a compound of Formula I-VII, or a pharmaceutically acceptable salt or prodrug thereof, and a pharmaceutically acceptable vehicle.

The invention encompasses methods of treating or preventing diseases and disorders described herein by administering a composition or formulation comprising a compound of Formula VII:

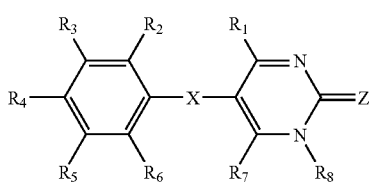

VII wherein each of $R_1$, $R_2$, $R_3$, $R_4$, $R_5$, $R_6$, and $R_7$ are independently a hydrogen, alkoxy, alkyl, alkenyl, alkynyl, aryl, aryloxy, benzyl, cycloalkyl, halogen, heteroaryl, heterocycloalkyl, —CN, —OH, —NO$_2$, —CF$_3$, —CO$_2$H, —CO$_2$alkyl, or —NH$_2$;

$R_8$ is an alkyl or hydrogen;

X is O, S, NH, or N-alkyl; and

Z is O or S.

In one illustrative embodiment, $R_8$ is alkyl, preferably methyl.

In another illustrative embodiment, $R_8$ is a hydrogen.

In another illustrative embodiment, X is oxygen.

In another illustrative embodiment, Z is oxygen.

In another illustrative embodiment, at least one of $R_2$-$R_6$ is alkyl, preferably methyl.

In another illustrative embodiment, at least one of $R_2$-$R_6$ is halogen, preferably chloro.

In another illustrative embodiment, at least one of $R_2$-$R_6$ is —CN.

In another illustrative embodiment, at least one of $R_2$-$R_6$ is —OH.

In another illustrative embodiment, at least one of $R_2$-$R_6$ is —NO$_2$.

In another illustrative embodiment, at least one of $R_2$-$R_6$ is —CF$_3$.

In another illustrative embodiment, at least one of $R_2$-$R_6$ is —CO$_2$H.

In another illustrative embodiment, at least one of $R_2$-$R_6$ is —NH$_2$.

In another illustrative embodiment, at least one of $R_2$-$R_6$ is -alkoxy.

In another illustrative embodiment, $R_2$ is alkyl, preferably methyl and each of $R_1$, and $R_3$-$R_8$ is hydrogen and X and Z are O.

In another illustrative embodiment, $R_2$ is a halogen, preferably chloro, and each of $R_1$, and $R_3$-$R_8$ is hydrogen and X and Z are O.

In another illustrative embodiment, $R_3$ is alkyl, preferably methyl and each of $R_1$, $R_2$ and $R_4$-$R_8$ is hydrogen and X and Z are O.

In another illustrative embodiment, $R_3$ is a halogen, preferably chloro, and each of $R_1$, $R_2$, and $R_4$-$R_8$ is hydrogen and X and Z are O.

In another illustrative embodiment, $R_4$ is alkyl, preferably methyl and each of $R_1$-$R_3$, and $R_5$-$R_8$ is hydrogen and X and Z are O.

In another illustrative embodiment, $R_4$ is a halogen, preferably chloro, and each of $R_1$-$R_3$, and $R_5$-$R_8$ is hydrogen and X and Z are O.

In another illustrative embodiment, $R_5$ is —CF$_3$, and each of $R_1$-$R_4$ and $R_6$-$R_8$ is hydrogen and X and Z are O.

In another illustrative embodiment, $R_5$—NH$_2$, and each of $R_1$-$R_4$ and $R_6$-$R_8$ is hydrogen and X and Z are O.

In another illustrative embodiment, $R_6$ is —CF$_3$, and each of $R_1$-$R_5$ and $R_7$-$R_8$ is hydrogen and X and Z are O.

In another illustrative embodiment, $R_6$ is —NH$_2$ and each of $R_1$-$R_5$ and $R_7$-$R_8$ is hydrogen and X and Z are O.

Illustrative examples of compounds that are encompassed by Formulas I-VII and that are useful in the methods of the invention include, but are not limited to:

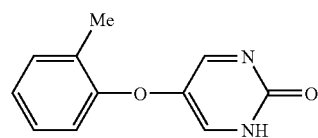

101

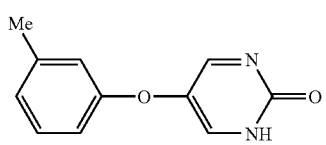

102

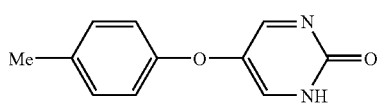

103

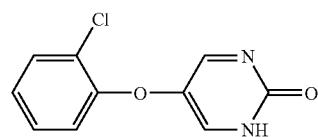

104

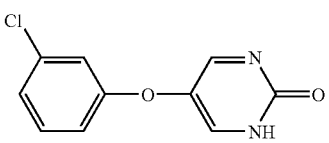

105

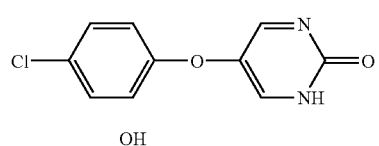

106

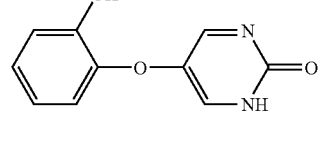

107

-continued

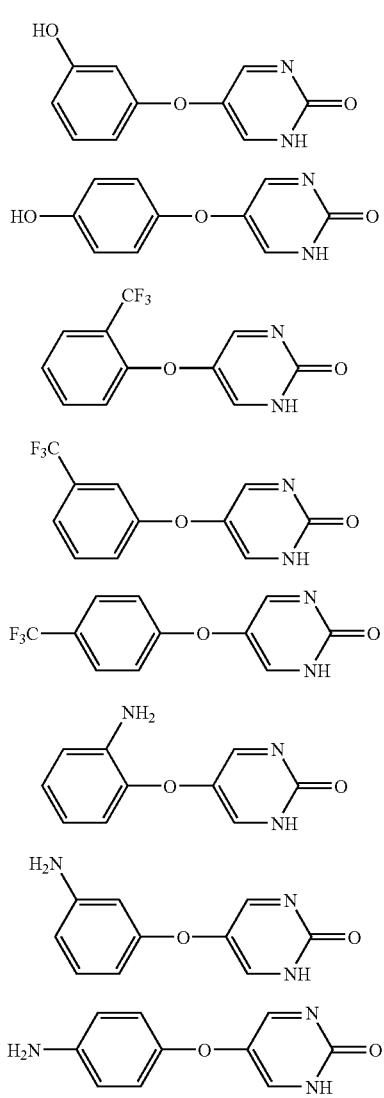

It will be understood that above compounds are illustrative only and not intended to limit the scope of the claims to only those compounds.

The compounds of the invention can be synthesized by organic chemistry techniques known to those of ordinary skill in the art, for example as described in U.S. Pat. No. 3,922,345, which is incorporated herein by reference in its entirety.

5.3. Therapeutic Uses of the Compounds of the Invention

The invention encompasses compounds that are effective in modulating the expression and/or activity of lyn kinase both in vitro and in vivo. The inventors have surprisingly found that the compounds of the invention are effective in modulating lyn kinase. Without being limited by theory, it is believed that modulation of lyn kinase expression and/or activity is useful in treating or preventing a disorder associated with abnormal blood glucose levels, weight gain, or fat depot levels. The invention further encompasses compositions and formulations comprising one or more compounds that are useful in modulating lyn kinase activity. The invention also encompasses methods of modulating lyn kinase activity comprising administering subject, preferably to a mammal including a human in need of said treatment or prevention a therapeutically or prophylactically effective amount of an agent described herein to modulate the activity of lyn kinase. In an illustrative embodiment, the agent for modulating lyn kinase activity is a compound of the invention.

In one embodiment, a composition of the invention comprising a compound of the invention and a pharmaceutically acceptable vehicle, is administered to a mammal, preferably a human, with a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence.

In one embodiment, "treatment" or "treating" refers to an amelioration of a disease or disorder, or at least one discernible symptom thereof, preferably associated with lyn kinase. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human having a genetic predisposition to a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence. Examples of such genetic predispositions include, but are not limited to, the ε4 allele of apolipoprotein E; a loss of function or null mutation in the lipoprotein lipase gene coding region or promoter (e.g., mutations in the coding regions resulting in the substitutions D9N and N291 S; for a review of genetic mutations in the lipoprotein lipase gene that increase the risk of cardiovascular diseases, dyslipidemias and dyslipoproteinemias, see, e.g., Hayden and Ma, 1992, *Mol. Cell Biochem.* 113:171-176); and familial combined hyperlipidemia and familial hypercholesterolemia.

In another illustrative mode of the embodiment, the compositions of the invention are administered as a preventative measure to a subject having a non-genetic predisposition to a cardiovascular disease, a dyslipidemia, a dyslipoproteinemia, a disorder of glucose metabolism, metabolic syndrome (i.e., Syndrome X), a PPAR-associated disorder, septicemia, a thrombotic disorder, type II diabetes, obesity, pancreatitis, hypertension, a renal disease, inflammation, or impotence. Examples of such non-genetic predispositions include, but are not limited to, cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease). In one particular embodiment, the methods of the invention do not encompass treating or preventing asthma.

5.3.1. Cardiovascular Diseases for Treatment or Prevention

The present invention provides methods for the treatment or prevention of a cardiovascular disease, comprising administering to a patient a therapeutically effective amount of a composition comprising a compound of the invention and a pharmaceutically acceptable vehicle. In some embodiments, the cardiovascular disease is associated with abnormal/altered lyn kinase activity and/or expression. As used herein, the term "cardiovascular diseases" refers to diseases of the heart and circulatory system. These diseases are often associated with dyslipoproteinemias and/or dyslipidemias. Cardiovascular diseases, which the compositions of the invention are useful for preventing or treating include, but are not limited to, arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

5.3.2. Dyslipidemias for Treatment or Prevention

The present invention provides methods for the treatment or prevention of a dyslipidemia comprising administering to a patient a therapeutically effective amount of a composition comprising a compound of the invention and a pharmaceutically acceptable vehicle. In some embodiments, the dyslipidemia is associated with abnormal/altered lyn kinase activity and/or expression. As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters which are used to diagnose dyslipidemia can be found at the web site of the American Heart Association and that of the National Cholesterol Education Program of the National Heart, Lung and Blood Institute. At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g., β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, for example, reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a composition comprising a compound of the invention in an amount effective alter lipid metabolism.

5.3.3. Dyslipoproteinemias for Treatment or Prevention

The present invention provides methods for the treatment or prevention of a dyslipoproteinemia comprising administering to a patient a therapeutically effective amount of a composition comprising a compound of the invention and a pharmaceutically acceptable vehicle. As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias, which the compositions of the present invention are useful for preventing or treating include, but are not limited to, high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with type II diabetes, obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of RDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a composition comprising a compound of the invention in an amount effective to bring about said reduction, elevation or promotion, respectively.

5.3.4. Glucose Metabolism Disorders for Treatment or Prevention

The present invention provides methods for the treatment or prevention of a glucose metabolism disorder, comprising administering to a patient a therapeutically effective amount of a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art. In some embodiments, the glucose metabolism disorder is associated with abnormal/altered lyn kinase activity and/or expression.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; and high levels of blood insulin and/or glucose.

The present invention further provides methods for altering glucose metabolism in a patient, for example to increase insulin sensitivity and/or oxygen consumption of a patient, said methods comprising administering to the patient a composition comprising a compound of the invention in an amount effective to alter glucose metabolism.

5.3.5. PPAR Associated Disorders for Treatment or Prevention

The present invention provides methods for the treatment or prevention of a peroxisome proliferative activated receptor ("PPAR")-associated disorder, comprising administering to a patient a therapeutically effective amount of a composition comprising a compound of the invention and a pharmaceutically acceptable vehicle. In some embodiments, the PPAR-associated disorder is associated with abnormal/altered lyn kinase activity and/or expression. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

5.3.6. Renal Diseases for Treatment or Prevention

The present invention provides methods for the treatment or prevention of a renal disease, comprising administering to a patient a therapeutically effective amount of a composition comprising a compound of the invention and a pharmaceutically acceptable vehicle. In some embodiments, the renal disease is associated with abnormal/altered lyn kinase activity and/or expression. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal diseasemedullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.3.7. Treatment or Prevention of Metabolic Syndrome

As used herein, "treatment or prevention of Syndrome X or Metabolic Syndrome" encompasses treatment or prevention of a symptom associated with metabolic syndrome including, but not limited to, impaired glucose tolerance, hypertension and dyslipidemia and/or dyslipoproteinemia. In some embodiments, the metabolic syndrome is associated with abnormal/altered lyn kinase activity and/or expression Metabolic syndrome is characterized by a group of metabolic risk factors in a person. Risk factors that are associated with metabolic syndrome that can be treated or prevented by administering a composition comprising a compound of the invention include, but are not limited to, central obesity (i.e., excessive fat tissue in and around the abdomen); atherogenic dyslipidemia (blood fat disorders—mainly high triglycerides and low HDL cholesterol—that foster plaque buildups in artery walls); raised blood pressure (130/85 mmHg or higher); insulin resistance or glucose intolerance (the body can't properly use insulin or blood sugar); prothrombotic state (e.g., high fibrinogen or plasminogen activator inhibitor [–1] in the blood); and a proinflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildups in artery walls (e.g., stroke and peripheral vascular disease) and type 2 diabetes.

Metabolic syndrome is closely associated with a generalized metabolic disorder called insulin resistance, in which the body can't use insulin efficiently. This is why the metabolic syndrome is also called the insulin resistance syndrome.

Some people are genetically predisposed to insulin resistance. Acquired factors, such as excess body fat and physical inactivity, can elicit insulin resistance and the metabolic syndrome in these people. Most people with insulin resistance have central obesity. The biologic mechanisms at the molecular level between insulin resistance and metabolic risk factors aren't fully understood and appear to be complex.

The compositions comprising a compound of the invention are therefore useful in treating or preventing metabolic syndrome and disorders and risk factors associated with metabolic syndrome.

5.3.8. Treatment or Prevention of Diabetes

As used herein, "treatment or prevention of diabetes" encompasses treatment or prevention of a complication associated with type II diabetes including, but not limited to, retinopathy (i.e., blindness); neuropathy (i.e., nerve damage) which leads to foot ulcers, gangrene, and amputations; kidney damage, which leads to dialysis; and cardiovascular disease. In some embodiments, the type II diabetes is associated with abnormal/altered lyn kinase activity and/or expression.

Type II diabetes is associated with obesity and with aging. It is a lifestyle-dependent disease, and has a strong genetic component (concordance in twins is 80-90%). The problem seems not so much in insulin production, but that when the insulin reaches its target cells, it doesn't work correctly. Most Type II diabetes patients initially have high insulin levels along with high blood sugar. However, since sugar signals the pancreas to release insulin, Type II diabetics eventually become resistant to that signal and the endocrine-pancreas soon will not make enough insulin. These people end up managing the disease with insulin and they need much higher doses because they are resistant to it.

When a person takes in a high load of sugar, the sugar stimulates the pancreas to release insulin. The targets for insulin are muscle, fat, and liver cells. These cells have insulin receptor sites on the outside of the cell membrane. For most people, when insulin has bound to the receptors, a cascade of events begins, which leads to sugar being transported from the blood into the interior of the cell. In Type II diabetics, even when insulin is present on the cell membrane, the process doesn't work. The glucose is never taken up into the cell and remains in the bloodstream.

The liver is responsible for glucose production and insulin is the regulatory agent of production. A high blood sugar content causes the pancreas to release insulin, and the insulin should signal the liver to stop making sugars. But, in diabetics, there's resistance to that signal and the liver keeps producing glucose. Hyperglycemia leads to glucose toxicity.

It is not high blood sugar that is the disease process of diabetes, but complications from the high blood sugar. A major problem faced by doctors is that some people with high blood sugar feel fine; it's hard to treat diseases that are asymptomatic since most people don't want to take a pill for something that they do not feel bad about. The compositions comprising a compound of the invention are therefore useful in treating or preventing type II diabetes or complications arising from type II diabetes and disorders and risk factors associated with metabolic syndrome. Complications of diabetes include, but are not limited to, diabetic neuropathy, diabetic retinopathy, erectile dysfunction, and kidney disease and the compounds of the invention are useful in treating or preventing these complications.

5.3.9. Treatment or Prevention of Obesity

As used herein, "treatment or prevention of obesity" encompasses treatment or prevention of a complication associated with obesity. Complications of obesity include, but are not limited to, hypercholesterolemia, hypertension, dyslipidemia (for example, high total cholesterol or high levels of triglycerides), type 2 diabetes, coronary heart disease, stroke, gallbladder disease, osteoarthritis, sleep apnea and respiratory problems, and some cancers (endometrial, breast, and colon). In some embodiments, the obesity is associated with abnormal/altered lyn kinase activity and/or expression

5.3.10. Other Diseases for Treatment or Prevention

The present invention provides methods for the treatment or prevention of septicemia, thrombotic disorders, pancreatitis, hypertension, inflammation, and impotence, comprising administering to a patient a therapeutically effective amount of a composition comprising a compound of the invention and a pharmaceutically acceptable vehicle. In some embodiments, these disorders are associated with abnormal/altered lyn kinase activity and/or expression As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions of the invention can be administered to an individual to promote weight reduction of the individual.

5.4. Therapeutic/Prophylactic Administration and Compositions

Due to the activity of the compounds of the invention, the compounds are advantageously useful in veterinary and human medicine. As described in Section 5.3 above, the compounds of the invention are useful for the treatment or prevention of cardiovascular diseases, dyslipidemias, dyslipoproteinemias, glucose metabolism disorders, metabolic syndrome (i.e., Syndrome X), PPAR-associated disorders, septicemia, thrombotic disorders, type II diabetes, obesity, pancreatitis, hypertension, renal disease, inflammation, and impotence. In some embodiments, the subject has abnormal/altered lyn kinase activity and/or expression but does not exhibit or manifest any physiological symptoms associated with a lyn-kinase-related disease.

The invention provides methods of treatment and prophylaxis by administration to a patient of a therapeutically effective amount of a composition comprising a compound of the invention. The patient is a mammal, including, but not limited to, an animal such a cow, horse, sheep, pig, chicken, turkey, quail, cat, dog, mouse, rat, rabbit, guinea pig, etc., and is more preferably a human.

The present compositions, which comprise one or more compounds of the invention, are preferably administered orally. The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, A. R. Gennaro (Editor) Mack Publishing Co.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

It is preferred that the compositions of the invention be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific preferred embodiments of the invention, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds of the invention may also be demonstrated to be effective and safe using animal model systems.

Other methods will be known to the skilled artisan and are within the scope of the invention.

5.5. Combination Therapy

In certain embodiments of the invention, the compounds of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent. As many of the disorders for which the compounds of the invention are useful in treating are chronic disorders, in one embodiment combination therapy involves alternating between administering a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds of the invention include but are not limited to atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds of the invention include but are not limited to 5-((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates for use in combination with the compounds of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile-acid-binding resin. Bile-acid-binding resins for use in combination with the compounds of the invention include but are not limited to cholestyramine and colestipol hydrochloride.

The present compositions can also be administered together with niacin or nicotinic acid.

The present compositions can also be administered together with a RXR agonist. RXR agonists for use in combination with the compounds of the invention include but are not limited to LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, or 4-((3,5,5,8,8-pentamethyl-5,6,7,8-tetrahydro-2-naphthyl)2-carbonyl)-benzoic acid.

The present compositions can also be administered together with an anti-obesity drug. Anti-obesity drugs for use in combination with the compounds of the invention include but are not limited to β-adrenergic receptor agonists, preferably β-3 receptor agonists, sibutramine, bupropion, fluoxetine, and phentermine.

The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

The present compositions can also be administered together with a biguanide. Biguanides for use in combination with the compounds of the invention include but are not limited to metformin, phenformin and buformin.

The present compositions can also be administered together with an α-glucosidase inhibitor. α-glucosidase inhibitors for use in combination with the compounds of the invention include but are not limited to acarbose and miglitol.

The present compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. Nos. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an HDL-raising drug; an HDL enhancer; or a regulator of the apolipoprotein A-I, apolipoprotein A-IV and/or apolipoprotein genes.

5.5.1. Combination Therapy with Cardiovascular Drugs

The present compositions can be administered together with a known cardiovascular drug. Cardiovascular drugs for use in combination with the compounds of the invention to prevent or treat cardiovascular diseases include but are not limited to peripheral anti-adrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

5.5.2. Combination Therapy for Cancer Treatment

The present compositions can be administered together with treatment with irradiation or one or more chemotherapeutic agents. For irradiation treatment, the irradiation can be gamma rays or X-rays. For a general overview of radiation therapy, see Heilman, Chapter 12: Principles of Radiation Therapy Cancer, in: Principles and Practice of Oncology, DeVita et al., eds., $2^{nd}$. Ed., J.B. Lippencott Company, Philadelphia. Useful chemotherapeutic agents include methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention.

6. EXAMPLES

Type II diabetes is characterized by high blood glucose levels in the presence of normal amounts of insulin. Animal models of type II diabetes involve administering high levels of glucose and measuring blood glucose levels and the ability of the experimental animal to maintain glucose homeostasis over time. Several pharmacological structural classes can effectively regulate this hyperglycemic response including sulfonylureas, thiazoladinediones (PPARγ agonists; glitazones) or metformin (glucophage). These drug classes are also clinically approved for use in humans. In the current study, we established a mouse model of hyperglycemia by administering high levels of glucose to mice. We validated this as a model of type II diabetes by demonstrating that metformin can effectively reduce the blood glucose load. We demonstrate that Compound 102 and Compound 105, which are illustrative examples of compounds of the invention, are effective in reducing blood glucose levels in this model of type II diabetes.

6.1. Example 1

Oral Glucose Tolerance Test

Glucose was formulated in water at a concentration of 150 mg/ml and dosed at a volume of 10 ml/kg to produce a dose of 1.5 g/kg. Glucose was measured using the Ascensia II Elite XL glucose monitor (Bayer). Measure glucose by taking a small (2 mm) section off the tip of the tail, bleed onto glucose test strip and measure. Data for each time point analyzed by ANOVA and post-hoc Tukey's test. A p value of less then 0.05 was used to indicate statistical significance.

Two studies were conducted with the following Compound 102.

In study 1, mice were dosed with Compound 102 and glucose as follows:

| Time (minutes) | Treatment/measure |
| --- | --- |
| 0 | Drug or vehicle |
| 15 | Glucose measure |
| 30 | Administer oral glucose |
| 45 | Glucose measure |
| 60 | Glucose measure |
| 90 | Glucose measure |
| 120 | Glucose measure |

In study 2, mice were dosed with Compound 102 and glucose as follows.

| Time (minutes) | Treatment/measure |
| --- | --- |
| 0 | Administer Drug |
| 15 | Glucose measure |
| 30 | Drug or vehicle |
| 30 | Administer oral glucose |
| 45 | Glucose measure |
| 60 | Drug or vehicle |
| 75 | Glucose measure |
| 90 | Drug or vehicle |
| 120 | Glucose measure |
| 150 | Glucose measure |

Study 3 tested Compound 102 and was conducted as follows:

| Time (minutes) | Treatment/measure |
| --- | --- |
| 0 | Drug or vehicle |
| 15 | Glucose measure |
| 30 | Administer oral glucose |
| 45 | Glucose measure |
| 60 | Glucose measure |
| 90 | Glucose measure |
| 120 | Glucose measure |

In study 1, a single administration of Compound 102 at a dose of 30 mg/kg significantly decreased normal blood glucose levels (pre-glucose loading) and significantly attenuated the blood glucose levels produced by oral glucose administration. Significance was lost 90 minutes after drug administration.

In study 2, with increased dosing, Compound 102 produced a more dramatic effect on blood glucose levels.

Compounds 105 also produced dramatic reductions in blood glucose levels. A single dose of 2 or 10 mg/kg significantly ($P<0.05$) reduced blood glucose levels at all time points after administration. Baseline blood glucose levels were also significantly depressed. Data are shown in FIG. 3.

6.2. Example 2

Western Diet

Male CD1/ICR mice were obtained from Harlan. The study was started when mice were 8 weeks of age. Prior to initiation of the study mice fasted for 24 hrs. Mice were fed "Western Diet" that was designed to approximate the "typical" human diet of North America and Europe (Research Diets; New Brunswick, N.J.; Western Diet composition). The Western Diet contained greater then 5 times more fat then normal chow.

| Compound 102. Diet Compositions | | |
| --- | --- | --- |
| | Western Diet gm % | Normal Diet gm % |
| Protein | 20 | 16 |
| Carbohydrate | 50 | 61 |
| Fat | 21 | 4 |
| kcal/gm | 4.7 | 3.2 |

Mice were weighed daily beginning from the start of the 24 hr fasting period. Food intake was monitored continuously. Mice were bled by retroorbital eyebleed on days 7, 14, 21 and 28 after the initiation of the study. On day of REB mice were dosed 1× with full dose 1 hr prior to bleed. Fat pads were dissected at the end of the study (day 31) weighed and frozen. The following fat pads were dissected: brown, inguinal, axial, mesenteric, renal and epidydimal. Data were averaged and analyzed by ANOVA followed by a post-hoc Tukey's test with a p value of less then 0.05 indicating a statistical difference.

Administration of Compound 102 significantly reduced weight gain at the highest dose tested (30 mg/kg/day). This effect was apparent when measuring absolute weight (FIG. 1) and also when measuring weight change from day 0 (FIG. 2). Food intake was not affected by Compound 102 administration (FIG. 3).

Fat pads weights were significantly elevated in Western diet animals as compared to normal chow fed animals. Compound 102 administration significantly reduced brown, axial, inguinal, renal and epidydimal fat pad increases, but not mesenteric levels (FIG. 4)

Administration of Compound 102 produced a significant alteration in weight change in western diet fed animals that was independent of an effect on food intake and that was associated with reduction in fat pad development.

6.3. Example

3: Leptin Levels in Western Diet Treated Animals

Blood from mice that were on western diet (Compound 102) were analyzed for leptin levels. Mice were bled by retroorbital eyebleed on days 7, 14, 21 and 28 after the initiation of the study. On day of REB mice were dosed once with full dose 1 hr prior to bleed. Leptin levels were determined by ELISA (R&D Systems) as per directions. Data are expressed as the average ±SEM. Data were averaged and analyzed by ANOVA followed by a post-hoc Tukey's test with a p value of less then 0.05 indicating a statistical difference.

Western diet led to a significant reduction in blood leptin levels as early as one week after initiation of the study. These leptin levels were not different from leptin levels of animals fed a normal diet. Administration of Compound 102 to animals fed a western diet reduced leptin levels to those fed a normal diet. This reduction may reflect a decrease in fat pad development and may be secondary to this event.

These data taken together with the data on weight gain, food intake and fat pad development indicate that animals fed a western diet and treated with Compound 102 do not look different from those fed a normal diet.

6.4. Example 4

In Vivo Db/Db Mouse Study

Db/Db and Db/lean mice were obtained from Harlan at 6 weeks of age. Mice were housed 3 per cage and fed ad libitum normal rodent chow. Mice were kept on a 12 hr Light:dark cycle.

The study was initiated when mice reached an age of 8 weeks and their baseline blood glucose levels were greater than 200 mg/dl. Compound 102 was formulated in PBS: 2N HCl (99:1) at concentrations of 0.5, 1.5 and 5 mg/ml. Mice were dosed at volumes of 10 ml/kg to produce doses of 5, 15 and 50 mg/kg/dose. Mice were dosed twice per day at an 8 hr interval (8 am and 4 pm) during the light cycle.

6.4.1. Glucose Study

For the acute blood glucose measurements, blood glucose levels were measured after the animals received their first dose of Compound 102. Blood glucose levels were measured two hrs after this initial injection.

6.4.2. Obesity Study

Mice were administered vehicle or drug (i.e., Compound 102) (5, 15, and 50 mg/kg) twice per day (bid) for the 28 days. Mouse weight and food intake were monitored daily. Food intake is reported as food intake (grams) per mouse per 24 hr period.

6.4.3. Glucose Results

In a Db/Db Leptin Receptor deficient diabetes/metabolic syndrome animal model, Compound 102 exhibited a dose dependent effect on both animal weight gain and blood glucose levels. In this study, mice were dosed with Compound 102 IP, twice/day over the course of four weeks. Significantly different animal weights were observed between Db/Db vehicle treated mice and mice receiving Compound 102 at doses of 5 mg/kg, 15 mg/kg ($p<0.05$) and 50 mg/kg ($p<0.01$). Compound 102 has also been shown to reduce blood glucose levels following acute administration. Animals also demonstrated an acute dose response in the 15 mg/kg and 50 mg/kg dose groups upon study initiation and on weekly blood glucose testing.

6.4.4. Obesity Results

When chronically administered to mice, Compound 102 significantly inhibited a weight-gain response to animals fed a high fat diet. There is no obvious trivial explanation for this effect. Most importantly, animals demonstrated normal food 1 intake compared to vehicle-treated animals. Also, animals defecated normally and did not display the hyperactivity normally associated with the amphetamine class of weight-loss drugs.

6.5. Example 5

In Vivo Zucker Rat Study

Zucker rats and corresponding lean rats were supplied by Harlan. Rats were fed a normal diet, ad libitum, and kept on a 12 hr light/dark cycle. Rats were housed 3 per cage.

6.5.1. Glucose Study

At 12 weeks of age, Zucker rats were administered Compound 102 at a concentration of 30 mg/kg (ip). Blood glucose levels were measured 30 minutes after administration. Forty-five minutes after drug administration, animals were administered a glucose solution (1.5 g/kg) by oral gavage. Blood glucose levels were measured every 30 minutes after gavage for 4.5 hrs.

There were 3 groups with 3 animals per group: 1) 3 Zucker leans (no drug; no glucose treatment); 2) Zucker vehicle treated group (glucose challenged and 3) Zucker Compound 102 treatment (30 mg/kg); glucose challenged.

6.5.2. Glucose Results

Oral glucose administration produced an elevation of blood glucose levels at two time points after administration: 30 and 270 minutes. Administration of Compound 102 reduced blood glucose levels at both time points.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method of reducing blood glucose levels or weight gain or treating type II diabetes, obesity, or metabolic syndrome in a mammal comprising administering to the mammal in need thereof an effective amount of a composition comprising a compound of formula:

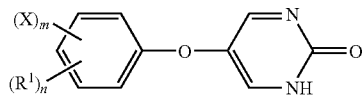

wherein $R^1$ is methyl and n is 1; X is a halogen; and m is 0 or 1, or a pharmaceutically acceptable salt thereof.

2. A method of reducing blood glucose levels or weight gain or treating type II diabetes, obesity, or metabolic syndrome in a mammal comprising administering to the mammal in need thereof an effective amount of a composition comprising a compound of formula:

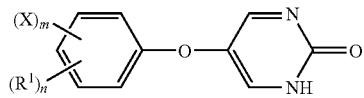

wherein X is chlorine and m is 1; $R^1$ is an alkyl group; and n is an integer from 0 to 5, wherein m+n is less than or equal to 5, or a pharmaceutically acceptable salt thereof.

3. A method of reducing blood glucose levels or weight gain or treating type II diabetes, obesity, or metabolic syndrome in a mammal comprising administering to the mammal in need thereof an effective amount of a composition comprising a compound of formula:

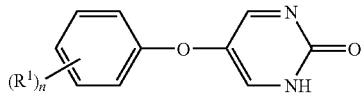

wherein R¹ is methyl, and n is 1, or a pharmaceutically acceptable salt thereof.

4. A method of reducing blood glucose levels or weight gain or treating type II diabetes, obesity, or metabolic syndrome in a mammal comprising administering to the mammal in need thereof an effective amount of a composition comprising a compound of formula:

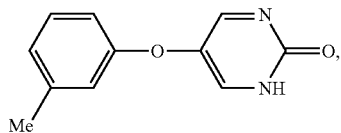

or a pharmaceutically acceptable salt thereof.

5. A method of reducing blood glucose levels or weight gain or treating type II diabetes, obesity, or metabolic syndrome in a mammal comprising administering to a mammal in need thereof an effective amount of a composition comprising a compound of formula:

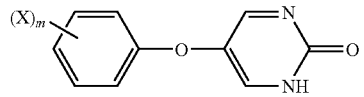

wherein X is chloro and m is 1, or a pharmaceutically acceptable salt thereof.

6. A method of reducing blood glucose levels or weight gain or treating type II diabetes, obesity, or metabolic syndrome in a mammal comprising administering to the mammal in need thereof an effective amount of a composition comprising a compound of formula:

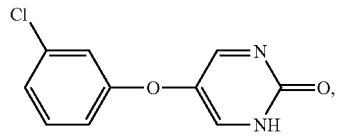

or a pharmaceutically acceptable salt thereof.

7. The method of claim 1 wherein the method is for reducing blood glucose levels.

8. The method of claim 1 wherein the method is for reducing weight gain.

9. The method of claim 8 wherein the composition further comprises rosiglitazone.

10. The method of claim 1 wherein the method is for treating type II diabetes.

11. The method of claim 1 wherein the method is for treating obesity.

12. The method of claim 1 wherein the method is for treating metabolic syndrome.

13. The method of claim 4 wherein the method is for reducing blood glucose levels.

14. The method of claim 4 wherein the method is for reducing weight gain.

15. The method of claim 14 wherein the composition further comprises rosiglitazone.

16. The method of claim 4 wherein the method is for treating type II diabetes.

17. The method of claim 4 wherein the method is for treating obesity.

18. The method of claim 4 wherein the method is for treating metabolic syndrome.

* * * * *